United States Patent [19]  
Fujii et al.

[11] Patent Number: 4,490,366  
[45] Date of Patent: Dec. 25, 1984

[54] 2'-DEOXY-5-FLUOROURIDINE DERIVATIVE AND A PROCESS FOR PRODUCING THE SAME AND AN ANTITUMOR AGENT COMPRISING THE SAME

[75] Inventors: Setsuro Fujii, Toyonaka; Eiichi Sakakibara, Kobe, both of Japan

[73] Assignee: Funai Pharmaceutical Ind., Ltd., Osaka, Japan

[21] Appl. No.: 419,014

[22] Filed: Sep. 16, 1982

Related U.S. Application Data

[62] Division of Ser. No. 068,340, Aug. 21, 1979.

[30] Foreign Application Priority Data

Sep. 5, 1978 [JP] Japan ................. 53-108955

[51] Int. Cl.³ .............................. A61K 31/70  
[52] U.S. Cl. ....................... 424/180; 536/23  
[58] Field of Search .................... 536/23; 424/180

[56] References Cited  
U.S. PATENT DOCUMENTS 3,309,359 3/1967 Duschinsky et al. ............ 536/23  
3,975,367 8/1976 Gish et al. ...................... 536/23  
4,055,716 10/1977 Ishida et al. .................... 536/23

Primary Examiner—Blondel Hazel  
Attorney, Agent, or Firm—Birch, Stewart, Kolasch & Birch

[57] ABSTRACT

A 2'-deoxy-5-fluorouridine derivative represented by the formula;

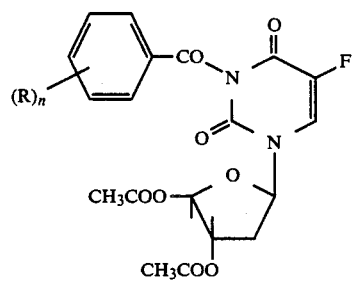

wherein R represents a hydrogen atom, an alkyl group having 1 to 5 carbon atoms, an alkoxy group having 1 to 4 carbon atoms, an acetyloxy group or a halogen atom, and n is an integer of 1 to 3.

2 Claims, No Drawings

2'-DEOXY-5-FLUOROURIDINE DERIVATIVE AND A PROCESS FOR PRODUCING THE SAME AND AN ANTITUMOR AGENT COMPRISING THE SAME

This application is a divisional of copending application Ser. No. 068,340, filed on Aug. 21, 1979.

BACKGROUND OF THE INVENTION

1. Field of the Invention

This invention relates to a novel 2'-deoxy-5-fluorouridine derivative represented by the general formula (I);

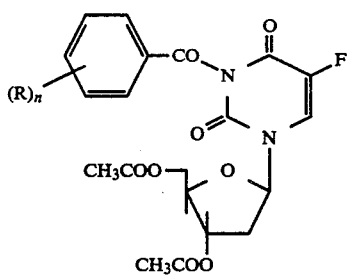

wherein R represents a hydrogen atom, an alkyl group having 1 to 5 carbon atoms, an alkoxy group having 1 to 4 carbon atoms, an acetyloxy group or a halogen atom, and n is an integer of 1 to 3, and to a process for producing the same, and further to an antitumor agent comprising the same as an active ingredient.

2. Description of the Prior Art

2'-Deoxy-5-fluorouridine (hereinafter referred to as "FUDR") is a compound used as an antitumor agent. However, FUDR is potentially a highly toxic drug with a narrow margin of safety. In addition, the administration route of FUDR is limited to the intra-arterial injection, that is, FUDR cannot be medicated by an oral route. This is definitely limiting to the clinical therapy [Physicians' Desk Refernece, 1387, (1978)].

C. Heidelberger el al have made an energetic study on the action mechanism of FUDR and have examined a variety of FUDR derivatives obtained by chemical modification of FUDR in order to make an improvement on the above defects and endow a greater antitumor effect.

As a result, it has been suggested that 2'-deoxy-3',5'-di-O-acetyl-5-fluorouridine (hereinafter referred to as "acetyl FUDR"), which is one of the FUDR derivatives synthesized by C. Heidelburger et al., may not be degraded easily in vivo when medicated orally [Cancer Research 23, 49(1963)]. However, the experimental results on the antitumor activity show that acetyl FUDR is nearly equal to, or may be less effective than FUDR [Biochemical Pharmacology 14, 1605(1965); Cancer Research 23, 420(1963)].

The results obtained by many studies on the FUDR derivatives are summarized in Cancer Research [30, 1555–1556(1970)] in terms of the relationships between the chemical structures of FUDR and derivatives thereof and the antitumor activities.

In this literature there is provided an illustration which indicates what type of groups at any position in the FUDR molecular structure is indispensable in manifestation of the antitumor effect, using, as an indicator, the three key enzymatic activities which have been found to be involved in the mechanism of the anticancer action of the FUDR derivatives. And there can be found an express mention that the nitrogen atom at the 3-position on the pyrimidine ring should not be substituted.

The present inventors have made an energetic study on acetyl FUDR derivatives in order to enhance their antitumor activities and to lower their toxicity, and as a result, have found, in contrast to the above conclusion, that a novel compound represented by the general formula (I) possesses a desirable effect, which is substituted at the nitrogen atom at the 3-position on the pyrimidine ring by a specified aroyl group.

DESCRIPTION OF THE PREFERRED EMBODIMENTS

In the definition of R in the formula (I), an alkyl group having 1 to 5 carbon atoms includes a straight-chain or branched alkyl group, such as methyl, ethyl, n-propyl, isopropyl, n-butyl, sec-butyl, tert-butyl, n-pentyl, isopentyl or the like. An alkoxy group having 1 to 4 carbon atoms includes a straight-chain or branched alkoxy group, such as methoxy, ethoxy, n-propoxy, isopropoxy, n-butoxy, sec-butoxy, tert-butoxy or the like. A halogen atom includes a fluorine, chlorine, bromine or iodine atom.

The compound of the formula (I) according to the present invention can be produced, for instance, by reacting 2-deoxy-3',5'-di-O-acetyl-5-fluorouridine with a benzoyl halide represented by the general formula (II):

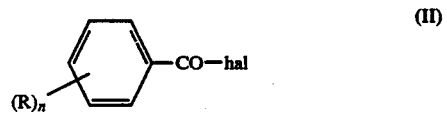

wherein hal represents a halogen atom, and R and n are the same as defined above.

Chloride or bromide is particularly preferable among the benzoyl halides used as a starting material.

One to 3 moles of the benzoyl halide is preferably employed against 1 mole of acetyl FUDR.

The reaction is usually conducted favorably in an organic solvent which includes an atropic solvent, such as ether, dioxane, chloroform, acetonitrile, pyridine or dimethylformamide.

In addition, the reaction is preferably carried out in the presence of an organic base, particularly trialkylamine or aromatic amine such as pyridine. Usually, the base is used in an amount of 1 to 5 moles against 1 mole of the benzoyl halide. However, larger amounts of the organic base can be used in the case where the base serves as a solvent.

The reaction proceeds from with ice-cooling to at the boiling point of the solvent, and the reaction time is desirably from 30 minutes to several hours.

The present product can be collected in purified form by filtrating the reaction mixture and concentrating the filtrate under reduced pressure to obtain the residue, which is either recrystallized or subjected to chromatography. In case a viscous oily substance is obtained, it is dissolved in a small amount of dimethylsulfoxide, and the resulting solution is added dropwise to water with stirring to obtain the present product as a solid.

The pharmacological test results of the thus obtained compounds are shown below.

(a) Test of Antitumor Activity

Method:

About 5 millions of sarcoma 180 tumor cells (successive cultivation was made in the peritoneum of ICR-male mice) were transplanted subcutaneously in the inguinal region of the ICR-male mice, 5 weeks old. 24 Hours later, the present compounds were forcibly administrated with oral sonde once a day for 7 consecutive days. The body weight of each animal was measured for successive days just prior to administration. The present compounds suspended in the solution of 1% Tween 80-physiological saline was given to each animal in the same volume of 0.1 ml/10 g of body weight. A control group was given only the same volume of the above solution. Administrated amounts were differentiated according to the species of the present compounds within a rough range of 1 mg/kg to 200 mg/kg. The administration amount of the identical compound was graded with 3 to 12 ranks. The identical compound was given to one group consisting of 6 animals. The control group was composed of 18 animals.

On the 8th day after transplantation, animals were depleted to death under anesthesia. Immediately after the excision of tumor tissue, the tumor weight was measured. The average values of tumor weights in each treated group (referred to as "T") and the average values of tumor weights in the control group (referred to as "C") were calculated, and the values of the administrated amounts corresponding to 0.70 and 0.50 of T/C values were estimated.

Results:

| Administrated compounds | | Values indicating T/C 0.70 (mg/kg) | Values indicating T/C 0.50 (mg/kg) |
| --- | --- | --- | --- |
| Present compounds [indicating R in the formula (I)] | Hydrogen | 45 | 79 |
| | 2-Methyl | 23 | 72 |
| | 3-Methyl | 20 | 66 |
| | 4-Methyl | 44 | 80 |
| | 2,3-Dimethyl | 37 | 71 |
| | 2,4,6-Trimethyl | 62 | — |
| | 2-Methoxy | 43 | 77 |
| | 4-Methoxy | 64 | 105 |
| | 2,3-Dimethoxy | 3 | 22 |
| | 4-Propoxy | 24 | 52 |
| | 4-Butoxy | 26 | 78 |
| | 2-Fluoro | 38 | — |
| | 3-Fluoro | 5 | 26 |
| | 4-Fluoro | 63 | 96 |
| | 2-Chloro | 50 | 70 |
| | 3-Chloro | 68 | — |
| | 3,5-Dichloro | 54 | 92 |
| | 2,4-Dichloro | 63 | — |
| Known compounds | FUDR | 58 | 106 |
| | Acetyl FUDR | 72 | 101 |

According to the literature [Pharmacometrics, 7, 1277–1292 (1973)], the values of T/C ranging from 0.70 to 0.51 were estimated to be slightly effective and the values less than 0.50 to be effective. Therefore, the smaller the values indicating T/C 0.70 or 0.50 are, the stronger the antitumor activities are.

From the above results, it can be seen that the present compounds are superior to the known compounds in their antitumor activities.

(b) Test of Toxicity

Toxic values were measured by the following method, in consideration of the cumulative toxicity, judging from the effects of the present compounds.

Method:

ICR-male mice (5 weeks old) were used, each group consisting of 10 animals.

The present compounds were forcibly administrated with oral sonde once a day for 7 consecutive days. The body weight of each animal was measured for consecutive days just prior to administration. The present compounds were given in the same volume of 0.1 ml/10 g of body weight, which were suspended in the solution of 1% Tween 80-physioiogical saline. Administrated amounts were differentiated according to the species of the present compounds within a rough range of 100 mg/kg to 800 mg/kg. Administration amount of the identical compound was graded with 5 ranks. The identical compound was given to one group of mice. On the 14th day after the commencement of administration, the death was judged and $LD_{10}$ was estimated by the Litchfield-Wilcoxon method.

Results:

| Administrated compounds | | $LD_{10}$ (mg/kg) |
| --- | --- | --- |
| Present compounds [indicating R in the formula (I)] | Hydrogen | 140 |
| | 2-Methyl | 173 |
| | 3-Methyl | 146 |
| | 2,3-Dimethyl | 156 |
| | 2-Methoxy | 135 |
| | 2,3-Dimethoxy | 129 |
| | 4-Propoxy | 134 |
| | 4-Butoxy | 157 |
| | 3-Fluoro | 170 |
| | 3,5-Dichloro | 148 |
| Known compounds | FUDR | 114 |
| | Acetyl FUDR | 136 |

The therapeutic indexes ($LD_{10}$ value/T/C 0.50 value) were calculated from the results (a) and (b) above, which are shown in the following.

| Administrated compounds | | Therapeutic indexes |
| --- | --- | --- |
| Present compounds [indicating R in the formula (I)] | Hydrogen | 1.77 |
| | 2-Methyl | 2.40 |
| | 3-Methyl | 2.21 |
| | 2,3-Dimethyl | 2.20 |
| | 2-Methoxy | 1.75 |
| | 2,3-Dimethoxy | 5.86 |
| | 4-Propoxy | 2.58 |
| | 4-Butoxy | 2.01 |
| | 3-Fluoro | 6.54 |
| | 3,5-Dichloro | 1.61 |
| Known compounds | FUDR | 1.08 |
| | Acetyl FUDR | 1.35 |
| | 5-FU* | 0.98 |

*The same test was made as in (a) and (b) on 5-fluorouracil, and the therapeutic index was calculated.

As can be seen from the above results, the present compounds possess a preferred antitumor activity in comparison with the known compounds.

The present compounds are administrated preferably in a dose of 100 to 1000 mg daily. Parenteral administrations such as intravenous injection and intrarectal medication by means of suppository are also possible with the present products, but an oral administration is particularly preferred.

Oral preparations to be used include tablets, capsules and liquids, each unit containing 30 to 500 mg of the present compound as an active ingredient.

In addition to the active ingredient, the tablets and capsules may contain other compositions. For instance, the vehicles to be used include lactose, corn starch, potato starch and microcrystalline cellulose; the combining agents to be used include acacia, gelatine, hydroxypropyl cellulose and potato starch; the lubricants to be used include magnesium stearate and talc; the disintegrators to be used include carboxymethyl cellulose, calcium, potato starch and corn starch. In liquid preparations, the usual solubilizing and suspending agents can be employed, particularly preferred is polyethylene glycol 200.

The invention is illustrated below in further detail with reference to certain specific Examples, but the invention is not limited to these Examples.

EXAMPLE 1

10.0 g of 2'-deoxy-3',5'-di-O-acetyl-5-fluorouridine and 10 ml of triethylamine were dissolved in 50 ml of dioxane, and the resulting mixture was cooled with ice. To the mixture was added 7.0 g of 2-methylbenzoyl chloride, and the resulting mixture was allowed to stand at room temperature for 30 minutes and then at 45° C. for 60 minutes. The crystals formed were filtered off, and the filtrate was concentrated under reduced pressure. The thus obtained oily residue was dissolved in 50 ml of ethanol by application of heat. After being cooled, the solution was inoculated, and there was obtained 2'-deoxy-3',5'-di-O-acetyl-5-fluoro-3-(2-methylbenzoyl)-uridine) as crystals. Recrystallization of the product from ethanol afforded 11.3% (yield: 84.0%) of colorless prismatic crystals having a melting point of 108° to 109° C. The structure of the product was supported by the absorption spectra and elemental analysis.

Infrared spectrum: $\nu_{C=O}^{CHCl_3}$ 1748, 1715, 1668 cm$^{-1}$,

Ultraviolet spectrum: $\lambda_{max}^{EtOH}$ 255 nm,

NMR: $\delta$(ppm, CDCl$_3$): uridine moiety 7.76 (d,H$_6$), 6.20 (broad-t, H$_{1'}$), near 2.4 (m, H$_2$), 5.10–5.26 (m, H$_{3'}$), 4.16–4.40 (m, H$_{4',5'}$), 2.07 (s,CH$_3$CO), 2.00 (s, CH$_3$CO), benzoyl moiety 7.58 (d, H$_6$), 7.12–7.54 (m, H$_{3,4,5}$), 2.62 (s, CH$_3$).

Elemental Analysis: as C$_{21}$H$_{21}$FN$_2$O$_8$, Calculated (%): C 56.25, H 4.72, N 6.25, Found (%): C 56.10, H 4.62, N 6.42.

EXAMPLE 2

500 mg of 2'-deoxy-3',5'-di-O-acetyl-5-fluorouridine was dissolved in 5 ml of dry pyridine, and the resulting solution was cooled with ice. To the solution was added 710 mg of 2-methylbenzoyl chloride, and the mixture was allowed to stand at room temperature for 100 minutes. The same procedure as in Example 1 gave 200 mg (yield: 29.5%) of 2'-deoxy-3',5'-di-O-acetyl-5-fluoro-3-(2-methylbenzoyl)uridine as crystals having a melting point of 108° to 109° C. This was identical with the crystals obtained in Example 1 by the mixed examination.

EXAMPLE 3

500 mg of 2'-deoxy-3'v5'-di-O-acetyl-5-fluorouridine and 0.76 ml of triethylamine were dissolved in 10 ml of dry chloroform, and the resulting solution was cooled with ice. To the solution was added 710 mg of 2-methylbenzoyl chloride, and the mixture was allowed to stand at room temperature for 120 minutes. The same procedure as in Example 1 gave 330 mg (yield: 48.7%) of 2'-deoxy-3',5'-di-O-acetyl-5-fluoro-3-(2-methylbenzoyl)uridine as crystals having a melting point of 108° to 109° C. This was identical with the crystals obtained in Example 1 by the mixed examination.

EXAMPLE 4

500 mg of 2'-deoxy-3',5'-di-O-acetyl-5-fluorouridine and 0.76 ml of triethylamine were dissolved in 10 ml of dry acetonitrile, and the resulting solution was cooled with ice. To the solution was added 710 mg of 2-methylbenzoyl chloride, and the mixture was allowed to stand at room temperature for 90 minutes. The same procuedre as in Example 1 gave 260 mg (yield: 38.4%) of 2'-deoxy-3',5'-di-O-acetyl-5-fluoro-3-(2-methylbenzoyl)uridine as crystals having a melting point of 108° to 109° C. This was identical with the crystals obtained in Examples 1 by the mixed examination.

EXAMPLE 5

500 mg of 2'-deoxy-3',5'-di-O-acetyl-5-fluorouridine and 0.76 ml of triethylamine were added to 20 ml of dry ether, and the resulting mixture was stirred. To the mixture was added 710 mg of 2-methylbenzoyl chloride, and the resulting mixture was stirred at room temperature for 6 hours. The mixture was subjected to thin-layer chromatography on silica gel, together with the product in Example 1 as an authentic compound, using a mixed solvent of chloroform/methanol (39/1), thereby indicating that in the mixture was formed 2'-deoxy-3',5'-di-O-acetyl-5-fluoro-3-(2-methylbenzoyl)uridine. The Rf value was 0.62.

EXAMPLE 6

500 mg of 2'-deoxy-3',5'-di-O-acetyl-5-fluorouridine and 0.76 ml of triethylamine were dissolved in 10 ml of dry dimethylformamide, and the resulting solution was cooled with ice. To this solution was added 710 mg of 2-methylbenzoyl chloride, and the resulting mixture was allowed to stand at room temperature for 90 minutes. The mixture was subjected to thin-layer chromatography on silica gel, and the formation of 2'-deoxy-3',5'-di-O-acetyl-5-fluoro-3-(2-methylbenzoyl)uridine was confirmed as in Example 5

EXAMPLE 7

15.0 g of 2'-deoxy-3',5'-di-O-acetyl-5-fluorouridine and 15 ml of triethylamine were dissolved in 75 ml of dry dioxane, and the resulting solution was cooled with ice. To the solution was added 13.6 g of 2,3-dimethoxybenzoyl chloride, and the resulting mixture was allowed to stand at room temperature for 30 minutes and then at 90° C. for 30 minutes. The crystals produced were filtered off, and the filtrate was concentrated under reduced pressure. To the oily residue was added 200 ml of ethanol. Upon heating, the mixture began to separate crystals while the oily residue was dissolved. After dissolving the oily residue completely, the mixture was cooled, and there was obtained 2'-deoxy-3',5'-di-O-acetyl-3-(2,3-dimethoxybenzoyl)-5-fluorouridine as crystals. Recrystallization of the product from ethanol afforded 19.65 g (yield: 88.4%) or colorless needles having a melting point of 139° to 141° C. The structure was supported by the absorption spectra and elemental analysis.

Infrared spectrum: $\nu_{C=O}^{CHCl_3}$ 1745, 1715, 1670 cm$^{-1}$.

Ultraviolet spectrum: $\lambda_{max}^{EtOH}$ 264, 327 nm.

NMR: δ(ppm, CDCl₃). uridine moiety 7.71 (d, H₆), 6.24 (broad-t, H₁'), near 2.4 (m, H₂'), 5.14–5.28 (m, H₃'), 4.16–4.43 (m, H₄',₅'), 2.11 (s, CH₃CO), 2.04 (s, CH₃CO), benzoyl moiety 7.54 (dd, H₆), 7.10–7.20 (m, H₄,₅), 3.85 (s, OCH₃) 3.83 (s, OCH₃).

Elemental Analysis: as $C_{22}H_{23}FN_2O_{10}$, Calculated (%): C 53.44 H 4.69 N 5.67, Found (%): C 53.17 H 4.92 N 5.80.

EXAMPLE 8

1.0 g of 2'-deoxy-3',5'-di-O-acetyl-5-fluorouridine and 0.76 ml of triethylamine were dissolved in 10 ml of dry dioxane, and the resulting solution was cooled with ice. To the solution was added 0.65 g of benzoyl chloride, and the resulting mixture was allowed to stand at room temperature for 60 minutes and then at 45° C. for 30 minutes. The crystals formed were filtered off, and the filtrate was concentrated under reduced pressure. The oily residue was purified by column chromatography on silica gel [column, diameter 3.5 cm; length, 21 cm; solvent, chloroform-methanol (99/1)]. The purified oily substance was dissolved in 10 ml of dimethylsulfoxide and added dropwise to 300 ml of water with vigorous agitation to be deposited as a solid. This solid was collected by filtration, washed sufficiently with water and dried at room temperature under reduced pressure. There was obtained 1.04 g (yield: 79.1%) of 3-benzoyl-2'-deoxy-3',5'-di-O-acetyl-5-fluorouridine as powder. The structure was supported by the absorption spectra and elemental analysis.

Infrared spectrum: $\nu_{C=O}^{CHCl_3}$ 1748, 1715, 1665 cm⁻¹.

Ultraviolet spectrum: $\lambda_{max}^{EtOH}$ 253 nm,

NMR: δ(ppm, CDCl₃): uridine moiety 7.82 (d, H₆), 6.31 (broad-t, H₁'), around 2.5 (m, H₂'), 5.16–5.35 (m, H₃'), 4.24–4.47 (m, H₄',₅'), 2.16 (s, CH₃CO), 2.07 (s, CH₃CO), benzoyl moiety 7.99 (d, H₂,₆), 7.46–7.81 (m, H₃,₄,₅).

Elemental Analysis: as $C_{20}H_{19}FN_2O_8$, Calculated (%): C 55.30, H 4.41, N 6.45, Found (%): C 55.52, H 4.48, N 6.63.

EXAMPLES 9–39

The same procedure was repeated as in Example 8, and there were obtained 2'-deoxy-3',5'-di-O-acetyl-5-fluorouridine derivatives which are shown in the following Table.

| Examples | R in the formula (I) | yield (%) | Elemental Analysis Molecular Formula Calculated (%); C,H,N Found (%); C,H,N | IR $\nu_{C=O}^{CHCl_3}$ cm⁻¹ | UV $\lambda_{max}^{EtOH}$ nm | NMR (CDCl₃) δ(ppm) uridine moiety | benzoyl moiety |
|---|---|---|---|---|---|---|---|
| 9 | 3-Methyl | 49 | $C_{21}H_{21}FN_2O_8$<br>56.25, 4.72, 6.25<br>56.20, 4.78, 6.07 | 1750<br>1720<br>1670 | 257 | 7.80(d,H₆),6.30(broad-t,H₁')<br>near 2.5 : (m,H₂'),5.18–5.35(m,H₃')<br>4.27–4.47 (m,H₄',₅')<br>2.14(s,CH₃CO),2.06(s,CH₃CO) | 7.69–7.92(m,H₂,₆)<br>7.30–7.63(m,H₄,₅)<br>2.40(s,CH₃) |
| 10 | 4-Methyl | 81 | $C_{21}H_{21}FN_2O_8$<br>56.25, 4.72, 6.25<br>56.32, 4.66, 6.42 | 1745<br>1715<br>1670 | 263 | 7.81(d,H₆), 6.32(broad-t,H₁')<br>near 2.5(m,H₂),5.19–5.37(m,H₃')<br>4.28–4.49(m,H₄',₅')<br>2.16(s,CH₃CO), 2.08(s,CH₃CO) | 7.87(d,H₂,₆)<br>7.38(d,H₃,₅)<br>2.44(s,CH₃) |
| 11 | 2,3-Dimethyl | 89 | $C_{22}H_{23}FN_2O_8$<br>57.14, 5.01, 6.06<br>57.15, 5.03, 5.74 | 1748<br>1718<br>1665 | 259 | 7.73(d,H₆), 6.25(broad-t,H₁')<br>near 2.4(m,H₂'),5.14–5.30(m,H₃')<br>4.22–4.43(m,H₄',₅')<br>2.12(s,CH₃CO),2.05(s,CH₃CO) | 7.01–7.50(m,H₄,₅,₆)<br>2.55(s,CH₃)<br>2.34(s,CH₃) |
| 12 | 2,4-Dimethyl | 93 | $C_{22}H_{23}FN_2O_8$<br>57.14, 5.01, 6.06<br>57.12, 5.09, 5.95 | 1745<br>1712<br>1668 | 264.5 | 7.78(d,H₆),6.30(broad-t,H₁')<br>near 2.5(m,H₂'),5.19–5.35(m,H₃')<br>4.25–4.49(m,H₄',₅')<br>2.14(s,CH₃CO),2.06(s,CH₃CO) | 7.52(d,H₆)<br>7.21(broad-s,H₃)<br>7.13(d,H₅)<br>2.66(s,CH₃)<br>2.36(s,CH₃) |
| 13 | 2,5-Dimethyl | 66 | $C_{22}H_{23}FN_2O_8$<br>57.14, 5.01, 6.06<br>57.18, 4.79, 5.89 | 1742<br>1715<br>1663 | 258.5 | 7.74(d,H₆),6.27(broad-t,H₁')<br>near 2.5(m,H₂'),5.18–5.34(m,H₃')<br>4.22–4.46(m,H₄',₅')<br>2.13(s,CH₃CO),2.06(s,CH₃CO) | 7.22–7.41(m,H₃,₄,₆)<br>2.60(s,CH₃)<br>2.31(s,CH₃) |
| 14 | 2,6-Dimethyl | 25 | $C_{22}H_{23}FN_2O_8$<br>57.14, 5.01, 6.06<br>57.49, 5.09, 5.93 | 1748<br>1720<br>1673 | 267 | 7.76(d,H₆),6.25(broad-t,H₁')<br>near 2.5 (m,H₂'),5.16–5.31(m,H₃')<br>4.21–4.47(m,H₄',₅')<br>2.11(s,CH₃CO),2.04(s,CH₃CO) | 7.03–7.41(m,H₃,₄,₅)<br>2.37(s,2 × CH₃) |
| 15 | 3,4-Dimethyl | 75 | $C_{22}H_{23}FN_2O_8$<br>57.14, 5.01, 6.06<br>57.13, 5.01, 6.04 | 1743<br>1718<br>1665 | 266.5 | 7.75(d,H₆),6.28(broad-t,H₁')<br>near 2.4(m,H₂'),5.13–5.28(m,H₃')<br>4.20–4.44(m,H₄',₅')<br>2.12(s,CH₃CO),2.05(s,CH₃CO) | 7.70(d,H₂)<br>7.64(dd,H₆)<br>7.27(d,H₅)<br>2.30(broad-s,2 × CH₃) |
| 16 | 3,5-Dimethyl | 54 | $C_{22}H_{23}FN_2O_8$<br>57.14, 5.01, 6.06<br>57.04, 4.97, 6.19 | 1748<br>1718<br>1670 | 262.5 | 7.75(d,H₆),6.27(broad-t,H₁')<br>near 2.4(m,H₂'),5.13–5.29(m,H₃')<br>4.20–4.44(m,H₄',₅')<br>2.12(s,CH₃CO),2.05(s,CH₃CO) | 7.51(broad-s,H₂,₆)<br>7.30(broad-s,H₄)<br>2.32(s,2 × CH₃) |
| 17 | 2,4,6-Trimethyl | 39 | $C_{23}H_{25}FN_2O_8$<br>57.98, 5.29, 5.88<br>58.07, 5.56, 5.93 | 1750<br>1718 (sh)<br>1675 | 272 | 7.75(d,H₆),6.27(broad-t,H₁')<br>near 2.5(m,H₂'),5.16–5.31(m,H₃')<br>4.22–4.44(m,H₄',₅') | 6.92(s,H₃,₅)<br>2.34(s,2 × CH₃)<br>2.27(s,CH₃) |

-continued

Structure (NMR reference):

Core structure showing positions:
- N3-C4(=O)-C5(F)=C6 ring with N1
- C2(=O) connecting N1 and N3
- N1 connected to CH(1')-CH2(2')-CH(3')(OCOCH3)-CH(4')-CH(5')(OCOCH3)-O (sugar with CH3CO groups at 3' and 5')
- Benzoyl group: R-C6H4-C(=O)- with positions 1-6

| Examples | R in the formula (I) | yield (%) | Elemental Analysis Molecular Formula Calculated (%); C,H,N Found (%); C,H,N | IR $\nu_{C=O}^{CHCl_3}$ cm$^{-1}$ | UV $\lambda_{max}^{EtOH}$ nm | NMR (CDCl$_3$) δ(ppm) | |
|---|---|---|---|---|---|---|---|
| 18 | 2-Ethyl | 82 | $C_{22}H_{23}FN_2O_8$ <br> 57.14, 5.01, 6.06 <br> 57.30, 5.24, 6.08 | 1748 <br> 1715 <br> 1665 | 256 | 7.73(d,H$_6$),6.22(broad-t,H$_1'$) <br> near 2.4:(m,H$_2'$),5.10–5.29(m,H$_3'$) <br> 4.20–4.41(m,H$_{4',5'}$) <br> 2.12(s,CH$_3$CO),2.05(s,CH$_3$CO) | 7.13–7.63(m,H$_{3,4,5,6}$) <br> 3.07(q,CH$_2$) <br> 1.29(t,CH$_3$) |
| 19 | 4-Isopropyl | 95 | $C_{23}H_{25}FN_2O_8$ <br> 57.98, 5.29, 5.88 <br> 57.72, 5.37, 6.00 | 1748 <br> 1715 <br> 1668 | 263.5 | 7.83(d,H$_6$),6.33(broad-t,H$_1'$) <br> near 2.5(m,H$_2'$),5.21–5.39(m,H$_3'$) <br> 4.28–4.51(m,H$_{4',5'}$) <br> 2.16(s,CH$_3$CO),2.08(s,CH$_3$CO) | 7.90(d,H$_{2,6}$) <br> 7.42(d,H$_{3,5}$) <br> 2.82–3.19(m,CH) <br> 1.27(d,2 × CH$_3$) |
| 20 | 4-tert-Butyl | 89 | $C_{24}H_{27}FN_2O_8$ <br> 58.77, 5.55, 5.71 <br> 58.61, 5.71, 5.37 | 1748 <br> 1715 <br> 1665 | 264 | 7.74(d,H$_6$),6.25(broad-t,H$_1'$) <br> near 2.5(m,H$_2'$),5.15–5.30(m,H$_3'$) <br> 4.20–4.43(m,H$_{4',5'}$) <br> 2.14(s,CH$_3$CO),2.07(s,CH$_3$CO) | 7.82(d,H$_{2,6}$) <br> 7.51(d,H$_{3,5}$) <br> 1.32(s,3 × CH$_3$) |
| 21 | 4-n-Pentyl | 29 | $C_{25}H_{29}FN_2O_8$ <br> 59.52, 5.79, 5.55 <br> 59.33, 5.86, 5.56 | 1745 <br> 1718 <br> 1667 | 264.5 | 7.80(d,H$_6$),6.28(broad-t,H$_1'$) <br> near 2.4(m,H$_2'$),5.16–5.33(m,H$_3'$) <br> 4.20–4.46(m,H$_{4',5'}$) <br> 2.12(s,CH$_3$CO),2.04(s,CH$_3$CO) | 7.85(d,H$_{2,6}$) <br> 7.33(d,H$_{3,5}$) <br> 2.65(t,CH$_2$) <br> 1.18–1.87(m,3 × CH$_2$) <br> 0.88(t,CH$_3$) |
| 22 | 2-Methoxy | 84 | $C_{21}H_{21}FN_2O_9$ <br> 54.31, 4.56, 6.03 <br> 54.52, 4.71, 6.18 | 1748 <br> 1715 <br> 1668 | 257.5 <br> 311.5 | 7.70(d,H$_6$),6.27(broad-t,H$_1'$) <br> near 2.4(m,H$_2'$),5.15–5.30(m,H$_3'$) <br> 4.17–4.45(m,H$_{4',5'}$) <br> 2.12(s,CH$_3$CO),2.05(s,CH$_3$CO) | 8.07(dd,H$_6$) <br> 7.60(td,H$_4$) <br> 7.07(t,H$_5$) <br> 6.94(d,H$_3$) <br> 3.78(s,OCH$_3$) |
| 23 | 4-Methoxy | 51 | $C_{21}H_{21}FN_2O_9$ <br> 54.31, 4.56, 6.03 <br> 54.25, 4.79, 6.24 | 1750 <br> 1715 <br> 1673 | 286 | 7.75(d,H$_6$),6.26(broad-t,H$_1'$) <br> near 2.4(m,H$_2'$),5.14–5.30(m,H$_3'$) <br> 4.22–4.44(m,H$_{4',5'}$) <br> 2.13(s,CH$_3$CO),2.06(s,CH$_3$CO) | 7.86(d,H$_{2,6}$) <br> 6.95(d,H$_{3,5}$) <br> 3.87(s,OCH$_3$) |
| 24 | 2,4-Dimethoxy | 60 | $C_{22}H_{23}FN_2O_{10}$ <br> 53.44, 4.69, 5.67 <br> 53.61, 4.70, 5.51 | 1740 <br> 1705 (sh) <br> 1663 | 277 <br> 314 | 7.68(d,H$_6$),6.28(broad-t,H$_1'$) <br> near 2.4 (m,H$_2'$),5.13–5.30(m,H$_3'$) <br> 4.18–4.41(m,H$_{4',5'}$) <br> 2.12(s,CH$_3$CO),2.05(s,CH$_3$CO) | 8.04(d,H$_6$) <br> 6.58(dd,H$_5$) <br> 6.38(d,H$_3$) <br> 3.84(s,OCH$_3$) <br> 3.74(s,OCH$_3$) |
| 25 | 3,4,5-Trimethoxy | 58 | $C_{22}H_{23}FN_2O_{11}$ <br> 52.67, 4.80, 5.34 <br> 52.87, 4.75, 5.35 | 1743 <br> 1713 <br> 1668 | 285 | 7.76(d,H$_6$),6.26(broad-t,H$_1'$) <br> near 2.5(m,H$_2'$),5.13–5.33(m,H$_3'$) <br> 4.18–4.48(m,H$_{4',5'}$) <br> 2.14(s,CH$_3$CO),2.06(s,CH$_3$CO) | 7.16(s,H$_{2,6}$) <br> 3.93(s,OCH$_3$) <br> 3.88(s,2 × OCH$_3$) |
| 26 | 2-Ethoxy | 89 | $C_{22}H_{23}FN_2O_8$ <br> 55.23, 4.85, 5.85 <br> 55.04, 4.99, 5.86 | 1740 <br> 1708 <br> 1665 | 258 <br> 323 | 7.68(d,H$_6$),6.28(broad-t,H$_1'$) <br> near 2.5(m,H$_2'$),5.15–5.31(m,H$_3'$) <br> 4.22–4.43(m,H$_{4',5'}$) <br> 2.11(s,CH$_3$CO),2.04(s,CH$_3$CO) | 8.08(dd,H$_6$) <br> 7.56(td,H$_4$) <br> 7.05(t,H$_5$) <br> 6.92(d,H$_3$) <br> 4.03(q,OCH$_2$),1.27(t,CH$_3$) |
| 27 | 4-Ethoxy | 60 | $C_{22}H_{23}FN_2O_9$ <br> 55.23, 4.85, 5.85 <br> 54.98, 5.00, 5.90 | 1740 <br> 1710 <br> 1668 | 287.5 | 7.76(d,H$_6$),6.28(broad-t,H$_1'$) <br> near 2.4:(m,H$_2'$),5.15–5.30(m,H$_3'$) <br> 4.20–4.42(m,H$_{4',5'}$) <br> 2.14(s,CH$_3$CO),2.07(s,CH$_3$CO) | 7.87(d,H$_{2,6}$) <br> 6.94(d,H$_{3,5}$) <br> 4.12(q,OCH$_2$) <br> 1.44(t,CH$_3$) |
| 28 | 4-n-Propoxy | 65 | $C_{23}H_{25}FN_2O_9$ <br> 56.10, 5.12, 5.69 <br> 55.87, 5.27, 5.78 | 1745 <br> 1712 <br> 1665 | 288 | 7.76(d,H$_6$),6.28(broad-t,H$_1'$) <br> near 2.4:(m,H$_2'$),5.16–5.31(m,H$_3'$) <br> 4.23–4.44(m,H$_{4',5'}$) <br> 2.14(s,CH$_3$CO),2.07(s,CH$_3$CO) | 7.87(d,H$_{2,6}$) <br> 6.95(d,H$_{3,5}$) <br> 4.01(t,OCH$_2$) <br> 1.63–1.98(m,CH$_2$) <br> 1.04(t,CH$_3$) |
| 29 | 4-n-Butoxy | 30 | $C_{24}H_{27}FN_2O_9$ <br> 56.91, 5.37, 5.53 <br> 57.00, 5.72, 5.67 | 1745 <br> 1713 <br> 1665 | 287.5 | 7.76(d,H$_6$),6.25(broad-t,H$_1'$) <br> near 2.4(m,H$_2'$),5.13–5.30(m,H$_3'$) <br> 4.22–4.43(m,H$_{4',5'}$) <br> 2.10(s,CH$_3$CO),2.03(s,CH$_3$CO) | 7.86(d,H$_{2,6}$) <br> 6.95(d,H$_{3,5}$) <br> 4.04(t,OCH$_2$) <br> 1.27–1.92(m,2 × CH$_2$) <br> 0.97(t,CH$_3$) |
| 30 | 2-Fluoro | 73 | $C_{20}H_{18}F_2N_2O_8$ <br> 53.10, 4.01, 6.19 <br> 52.86, 4.01, 6.10 | 1752 <br> 1720 <br> 1675 | 249.5 | 7.76(d,H$_6$),6.25(broad-t,H$_1'$) <br> near 2.5 (m,H$_2'$),5.17–5.32(m,H$_3'$) <br> 4.25–4.42(m,H$_{4',5'}$) <br> 2.14(s,CH$_3$CO),2.07(s,CH$_3$CO) | 8.08(td,H$_6$) <br> 7.03–7.75(m,H$_{3,4,5}$) |
| 31 | 3-Fluoro | 81 | $C_{20}H_{18}F_2N_2O_8$ <br> 53.10, 4.01, 6.19 <br> 53.13, 4.13, 6.15 | 1748 <br> 1720 <br> 1670 | 250.5 | 7.82(d,H$_6$),6.27(broad-t,H$_1'$) <br> near 2.4 (m,H$_2'$),5.16–5.34(m,H$_3'$) <br> 4.22–4.44(m,H$_{4',5'}$) <br> 2.12(s,CH$_3$CO),2.05(s,CH$_3$CO) | 7.30–7.88(m,H$_{2,4,5,6}$) |

| Examples | R in the formula (I) | yield (%) | Elemental Analysis Molecular Formula Calculated (%); C,H,N Found (%); C,H,N | IR $\nu_{C=O}^{CHCl_3}$ cm$^{-1}$ | UV $\lambda_{max}^{EtOH}$ nm | NMR (CDCl$_3$) δ(ppm) sugar/base | NMR aromatic |
|---|---|---|---|---|---|---|---|
| 32 | 4-Fluoro | 84 | C$_{20}$H$_{18}$F$_2$N$_2$O$_8$<br>53.10, 4.01, 6.19<br>52.89, 4.21, 6.23 | 1750<br>1718<br>1670 | 255 | 7.82(d,H$_6$),6.27(broad-t,H$_1$')<br>near 2.5 (m,H$_2$'),5.17–5.31(m,H$_3$')<br>4.22–4.46(m,H$_4$',$_5$')<br>2.13(s,CH$_3$CO),2.06(s,CH$_3$CO) | 8.00(dd,H$_{2,6}$)<br>7.22(t,H$_{3,5}$) |
| 33 | 2-Chloro | 67 | C$_{20}$H$_{18}$ClFN$_2$O$_8$<br>51.24, 3.87, 5.97<br>51.32, 3.91, 5.76 | 1748<br>1720<br>1672 | 255 | 7.82(d,H$_6$),6.28(broad-t,H$_1$')<br>near 2.5 (m,H$_2$'),5.18–5.35(m,H$_3$')<br>4.24–4.47(m,H$_4$',$_5$')<br>2.14(s,CH$_3$CO),2.06(s,CH$_3$CO) | 7.98(dd,H$_6$)<br>7.29–7.66(m,H$_{3,4,5}$) |
| 34 | 3-Chloro | 57 | C$_{20}$H$_{18}$ClFN$_2$O$_8$<br>51.24, 3.87, 5.97<br>51.00, 3.95, 5.95 | 1748<br>1718<br>1674 | 253.5 | 7.78(d,H$_6$),6.25(broad-t,H$_1$')<br>near 2.5(m,H$_2$'),5.16–5.31(m,H$_3$')<br>4.23–4.45(m,H$_4$',$_5$')<br>2.13(s,CH$_3$CO),2.06(s,CH$_3$CO) | 7.40–7.96(m,H$_{2,4,5,6}$) |
| 35 | 4-Chloro | 71 | C$_{20}$H$_{18}$ClFN$_2$O$_8$<br>51.24, 3.87, 5.97<br>51.49, 3.74, 5.91 | 1750<br>1720<br>1673 | 263 | 7.78(d,H$_6$),6.25(broad-t,H$_1$')<br>near 2.4(m,H$_2$'),5.15–5.31(m,H$_3$')<br>4.23–4.44(m,H$_4$',$_5$')<br>2.14(s,CH$_3$CO),2.07(s,CH$_3$CO) | 7.85(d,H$_{2,6}$)<br>7.50(d,H$_{3,5}$) |
| 36 | 2,4-Dichloro | 92 | C$_{20}$H$_{17}$Cl$_2$FN$_2$O$_8$<br>47.73, 3.41, 5.57<br>47.53, 3.63, 5.46 | 1745<br>1718<br>1675 | 263.5 | 7.74(d,H$_6$),6.21(broad-t,H$_1$')<br>near 2.4(m,H$_2$'),5.14–5.30(m,H$_3$')<br>4.22–4.45(m,H$_4$',$_5$')<br>2.12(s,CH$_3$CO),2.05(s,CH$_3$CO) | 7.82(d,H$_6$)<br>7.50(d,H$_3$)<br>7.39(dd,H$_5$) |
| 37 | 3,5-Dichloro | 59 | C$_{20}$H$_{17}$Cl$_2$FN$_2$O$_8$<br>47.73, 3.41, 5.57<br>47.30, 3.13, 5.38 | 1748<br>1720<br>1675 | 258 | 7.80(d,H$_6$),6.26(broad-t,H$_1$')<br>near 2.5(m,H$_2$'),5.16–5.32(m,H$_3$')<br>4.24–4.47(m,H$_4$',$_5$')<br>2.14(s,CH$_3$CO),2.07(s,CH$_3$CO) | 7.62–7.82(m,H$_{2,4,6}$) |
| 38 | 3-Bromo | 90 | C$_{20}$H$_{18}$BrFN$_2$O$_8$<br>46.80, 3.53, 5.46<br>46.53, 3.73, 5.01 | 1748<br>1720<br>1672 | 255 | 7.80(d,H$_6$),6.25(broad-t,H$_1$')<br>near 2.5 (m,H$_2$'),5.18–5.36(m,H$_3$')<br>4.22–4.47(m,H$_4$',$_5$')<br>2.14(s,CH$_3$CO),2.06(s,CH$_3$CO) | 8.05(broad-s,H$_2$)<br>7.76–7.95(m,H$_{4,6}$)<br>7.41(t,H$_5$) |
| 39 | 2-Acetyloxy | 60 | C$_{22}$H$_{21}$FN$_2$O$_{10}$<br>53.66, 4.30, 5.69<br>53.75, 4.56, 5.69 | 1750<br>1720<br>1675 | 253 | 7.62–8.00(H$_6$),6.30(broad-t,H$_1$')<br>near 2.4(m,H$_2$'),5.18–5.36(m,H$_3$')<br>4.20–4.56(m,H$_4$',$_5$')<br>2.14(s,CH$_3$CO),2.06(s,CH$_3$CO) | 7.62–8.00(m,H$_{4,6}$)<br>7.38(t,H$_5$)<br>7.26(d,H$_3$)<br>2.31(s,CH$_3$CO) |

EXAMPLE 40

500 mg of 2'-deoxy-3',5'-di-O-acetyl-5-fluorouridine and 0.76 ml of triethylamine were dissolved in 10 ml of dry dioxane, and the resulting mixture was cooled with ice. To the mixture was added 850 mg of benzoyl bromide, and the resulting mixture was allowed to stand at room temeprature for 15 minutes and then at 70° C. for 30 minutes. The same procedure as in Example 8 gave 400 mg (yield: 60.5%) of 3-benzoyl-2'-deoxy-3',5'-di-O-acetyl-5-fluorouridine. The absorption spectra of the present product were identical with those of the compound obtained in Example 8.

What we claim is:

1. A pharmaceutical composition containing an effective anti-tumor amount of 2'-deoxy-3',5'-di-O-acetyl-3-(3-methylbenzoyl)uridine as the active ingredient and a pharmaceutically acceptable carrier or diluent.

2. A method for treating tumors comprising administering to a host an effective anti-tumor amount of 2'-deoxy-3',5'-di-O-acetyl-3-(3-methylbenzoyl)uridine.

* * * * *